United States Patent [19]

Kaibel et al.

[11] Patent Number: 4,994,152

[45] Date of Patent: Feb. 19, 1991

[54] REMOVAL OF SMALL AMOUNTS OF A MEDIUM-BOILING FRACTION FROM A LIQUID MIXTURE BY DISTILLATION

[75] Inventors: Gerd Kaibel, Lampertheim; Karl Schloemer, Ludwigshafen; Hans-Horst Mayer, Speyer, all of Fed. Rep. of Germany

[73] Assignee: BASF Aktiengesellschaft, Ludwigshafen, Fed. Rep. of Germany

[21] Appl. No.: 457,943

[22] Filed: Dec. 27, 1989

[30] Foreign Application Priority Data

Jan. 25, 1989 [DE] Fed. Rep. of Germany ....... 3902006

[51] Int. Cl.$^5$ .............................................. B01D 3/00
[52] U.S. Cl. ...................................... 203/75; 203/77; 203/78; 203/80; 203/99; 203/DIG. 9; 203/DIG. 19; 568/338; 568/376
[58] Field of Search ....................... 203/75, 77, 78, 80, 203/99, DIG. 9, DIG. 19; 568/338, 376

[56] References Cited

U.S. PATENT DOCUMENTS

| | | | |
|---|---|---|---|
| 4,272,326 | 6/1981 | Hertzog et al. | 203/62 |
| 4,306,944 | 12/1981 | Murthy et al. | 203/80 |
| 4,448,644 | 5/1984 | Foster et al. | 203/DIG. 19 |
| 4,455,198 | 6/1984 | Zudkevitch et al. | 203/63 |
| 4,606,816 | 8/1986 | Harandi | 203/DIG. 19 |
| 4,662,995 | 5/1987 | Lipkin et al. | 203/DIG. 19 |
| 4,744,869 | 5/1988 | Saito et al. | 203/DIG. 19 |

FOREIGN PATENT DOCUMENTS

| | | | |
|---|---|---|---|
| 0132268 | 9/1978 | Fed. Rep. of Germany | 203/DIG. 19 |
| 0570371 | 8/1977 | U.S.S.R. | 203/DIG. 19 |

*Primary Examiner*—Virginia Manoharan
*Attorney, Agent, or Firm*—Keil & Weinkauf

[57] ABSTRACT

Small amounts of a medium-boiling fraction are removed from a liquid mixture by distillation using a distillation column (main column) having a rectifying part and a stripping part, the liquid mixture containing relatively large amounts of lower-boiling and higher-boiling components, and the rectifying part being connected to the upper end of a second distillation column (side column) and the stripping part to the lower end of the said column, and the medium-boiling fraction being removed in vapor or liquid form from its middle section, by a process in which the concentration of the medium-boiling fraction in the liquid mixture is less than 2%, preferably less than 0.1%, and the amount of vapor passed into the lower end of the side column from the main column is 1–20%, preferably 3–10%, based on the amount of vapor in the main column at the relevant point.

10 Claims, 1 Drawing Sheet

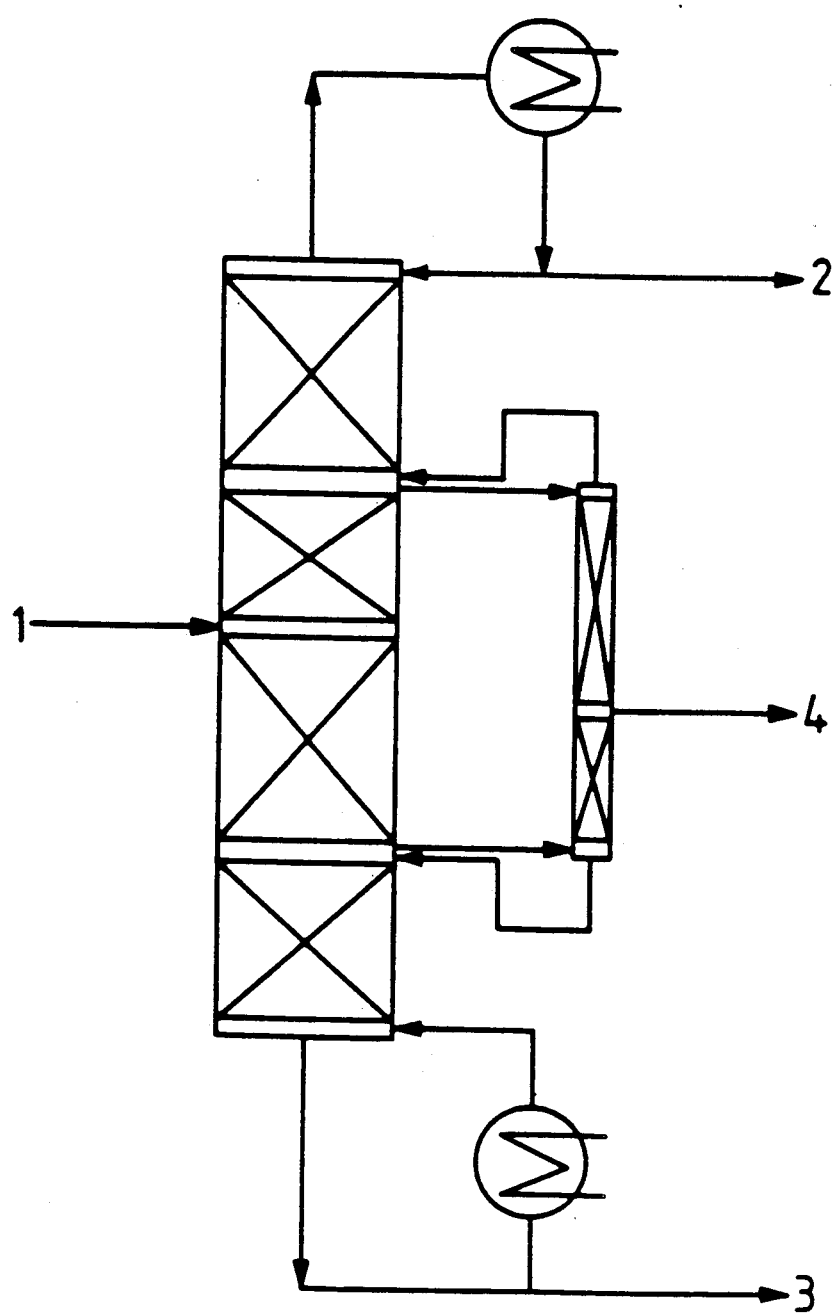

REMOVAL OF SMALL AMOUNTS OF A MEDIUM-BOILING FRACTION FROM A LIQUID MIXTURE BY DISTILLATION

The present invention relates to a process for the removal of small amounts of a medium-boiling fraction from a liquid mixture by distillation using a distillation column (main column) consisting of a rectifying part and a stripping part, the liquid mixture containing relatively large amounts of lower-boiling and higher-boiling components, and the rectifying part being connected to the upper end of a second distillation column (side column) by a liquid-phase line and the stripping part being connected to the lower end of this column by a vapor-phase line, and the medium-boiling fraction being removed in vapor or liquid form from its middle section.

An important basic operation in the chemical and petrochemical industries is the separation of multicomponent mixtures by distillation. A basic rule of distillation technology states that the separation of a feed mixture consisting of n components into pure individual fractions requires n−1 distillation columns. In the case of feed mixtures which are composed of a large number of individual fractions, this entails a technically very complicated process.

A particular problem consequently is that even the removal of impurities which are present in the feed mixture in only a low concentration, for example in a few ppm, but whose concentration in the desired fractions has to be decreased for quality reasons is very expensive since such separations too require a separate complete column unit. The dimensions of such a distillation plant and hence also the capital costs and the energy consumption are of the same order of magnitude as for column units for the removal of larger amounts of product.

To reduce the cost of the apparatus, it is usual to restrict operations, in the removal of small amounts of medium-boiling impurities, to simple withdrawal of a side stream and hence to dispense with the column unit. The disadvantage here is that high concentrations of the medium boiler are achievable in simple withdrawal of a side stream only with the use of large amounts of heat and the cost-efficiency is thus adversely affected. As a rule, high concentrations of medium boilers are therefore dispensed with and losses of low-boiling or high-boiling products ar accepted.

In the case of relatively high feed concentrations of the medium-boiling component, it is not possible to employ simple withdrawal of side streams for the stated reasons. Here, attempts are sometimes made to use side columns and by this measure to dispense with at least one heat exchanger, i.e. an evaporator or a condenser, depending on the type of column. However, there is scarcely any reduction in the energy requirement.

Relatively large energy savings and reductions in capital costs of about 30% are possible only with a partitioned column or the thermodynamically equivalent arrangement of a main column with a connected side column, in which the side column is connected both at its upper and at its lower end directly to the main column. These types of column permit the separation of a feed mixture into three pure components, only one evaporator and one condenser being required.

In the partitioned column and the thermodynamically equivalent arrangement of main and side columns, in general the vapors are preferably divided in a ratio of 1:1 between the feed part and the withdrawal part of the partitioned column or of the corresponding part columns in the form of separate column sections. This is desirable in a partitioned column for design reasons since it results in a simpler geometry of the column packing. Theoretical investigations too are concerned exclusively with demonstrating the usefulness of this uniform division of vapors between the two column sections.

The same applies to the alternative design in the form of two separate columns. Here too, uniform vapor division is preferred, and it is merely pointed out that in general only slightly more energy is involved if there is an unintentional deviation from the 1:1 division regarded as optimal. The tolerability of fluctuations in the vapor division between feed part and withdrawal part in the maximum range of from 1:3 to 3:1 is described as an advantage of this type of column. In principle, however, the 1:1 division will always be regarded as the most advantageous solution.

An important advantage of this column arrangement is thus unintentionally forfeited. The use of this type of column is therefore just as inflexible as that of the conventional columns, i.e. each individual distillation step of a process must be investigated beforehand in detail. Even the removal of small amounts of impurities must be clarified beforehand by exact investigations in pilot plants, and an appropriate distillative separation step must be planned and carried out separately in a conventional manner or using the modern types of columns described.

As found in practice, this is often difficult. In novel processes, it is frequently very difficult correctly to detect small amounts of impurities experimentally and correctly to determine their consequences with regard to apparatus prior to the construction of the production plant. It is therefore necessary, for example, to have a large number of recycling operations in pilot plants, resulting in a longer trial time, higher analytical requirements and hence greater costs. Furthermore, it is in any case impossible to detect all effects. New byproducts may occur during the production phase if, for example, a novel, more economical type of catalyst is used, starting materials of different origin are employed or other changes with regard to process engineering are made.

Frequently, such improvements in process engineering, and hence economic improvements, are not displayed since the additional removal of a component, even when it is present in only small amounts, necessitates an additional intermediate distillation step and, apart from the actual additional capital costs, therefore gives rise in particular to costs arising from shutdown for conversion, such costs generally being disproportionately higher.

It is an object of the present invention to remove small amounts of a medium-boiling fraction from a liquid mixture and to avoid all of the disadvantages described above.

We have found that this object is achieved, according to the invention, if the concentration of the medium-boiling fraction in the liquid mixture is less than 2%, preferably less than 0.1%, and the amount of vapor which is passed into the lower end of the side column from the main column is 1-20%, preferably 3-10%, based on the amount of vapor in the main column at the relevant point.

The subclaims relate to further features of the novel process.

Contrary to the opinion held to date, we have found that, in this case of the removal of small amounts, it is also possible to deviate from the 1:1 vapor division generally considered ideal, by charging the additional side column, which serves for removal of the medium-boiling byproduct, with only very small amounts of vapor of about 3–10%, based on the amount of vapor in the main column. Further, the liquid removed from the main column can be introduced at the upper end of the side column in an amount corresponding to 100–110% of the amount of vapor in the side column. This has the advantage that this side column gives rise to low capital and energy costs.

The separation into a low-boiling fraction and a high-boiling fraction in the main column is not adversely affected by this method. Since the concentration of the medium boiler in the main column is reduced by the connected side column, there are even slightly more advantageous separation efficiencies.

A particular advantage is that, in the novel removal of small amounts of medium boilers via a side column whose diameter is very small in relation to that of the main column, only small amounts of the low-boiling and high-boiling fraction are lost with the medium-boiling fraction in comparison with simple removal as a side stream.

There are no special requirements with regard to the number of theoretical plates in the side column, i.e. it may have the same number or a larger or smaller number of theoretical plates compared with the corresponding section of the main column. The type of packing too is independent of the main column. Since the side column has only a small cross-sectional area and hence entails low costs, it is generally equipped with a larger number of theoretical plates compared with the main column, about 20–50% more. Particularly, the side column may have a number of theoretical plates that is 100–200% of the number of plates in the section of the main column between the connections with the side column, preferably 120–140%.

The exact position of the connections to the main column in the rectifying part and stripping part depends on the separation specifications in the individual case and can be determined by computer simulation if the boiling properties of the medium-boiling impurities are known. Frequently, however, these physical properties are not known. In this case, and where the purity requirements are relatively stringent, the position of the connections is chosen between the main column and the side column so that they are closer to the feed point of the main column. In many cases, it proves advantageous to arrange the connections in the middle of the rectifying part and of the stripping part of the main column.

The arrangement of the side-stream withdrawal point on the side column should depend on the position of the feed point in the main column with respect to the connection points. In the case of location in the middle of the main column, it is preferable to arrange the side-stream withdrawal point in the side column likewise in the middle. If, however, the feed point is closer to the upper connection point, the withdrawal point should be closer to the lower connection point, and vice versa.

For example, the withdrawal point of the side column can be arranged in such a way that the ratio of the number of theoretical plates of the section of the main column between the feed point and the upper connection point to that between the feed point and the lower connection point is equal to the ratio of the numbers of theoretical plates of the sections of the side column below the withdrawal point to those above the withdrawal point.

In a further embodiment, the medium-boiling fraction can be removed in the form of a liquid and, at the withdrawal point of the fraction in the side column, the liquid can be kept for a residence time of from 0.1 to 2 hours in the column or in a separate container, and a side stream will be removed at the withdrawal point only periodically after appropriate analysis of the liquid.

In one preferred embodiment of the invention, the feed mixture contains from 40 to 65% by weight of cyclohexanone as the low-boiling fraction, from 0.001 to 0.5% by weight of methylcyclohexanone as the medium-boiling fraction and from 30 to 60% by weight of cyclohexanol and from 1 to 10% by weight of higher-boiling byproducts as the high-boiling fraction. The column is operated at a top pressure of from 0.01 to 1, preferably from 0.03 to 0.06, bar and with reflux ratio of from 1.2 to 6.0, preferably from 1.8 to 3.0. The number of theoretical plates of the main column is from 30 to 65, preferably from 40 to 50. The side column has from 30 to 80, preferably from 30 to 40, theoretical plates. A cyclohexanone fraction containing from 0.0001 to 0.02% by weight of methylcyclohexanone is removed at the top of the main column, a cyclohexanol fraction containing from 0.002 to 0.4% by weight of methylcyclohexanone is removed at the bottom of the main column and a medium-boiling fraction containing from 1 to 25% by weight of methylcyclohexanone is removed at the withdrawal of the side column.

BRIEF DESCRIPTION OF THE DRAWING

The drawing illustrates an apparatus for effecting the claimed process, including the main column and take-off column.

EXAMPLE (cf. drawing)

A feed mixture 1 consisting of 16,263 kg/h of cyclohexanone, 20,676.5 kg/h of cyclohexanol, 6.4 kg/h of methylcyclohexanone and 1,741.6 kg/h of higher-boiling byproducts is introduced in liquid form at 110° C. at the tenth theoretical plate of a distillation column having a total of 48 theoretical plates. The operating pressure of this column is 40 mbar at the top and 64 mbar at the bottom. At the top 2 of this column, 15,117 kg/h of cyclohexanone are removed at 62.3° C. and a reflux ratio of 2.9. The top product also contains 30 ppm of methylcyclohexanone. At the bottom 3, 1,128.7 kg/h of cyclohexanone, 20,671.3 kg/h of cyclohexanol, 4.25 kg/h of methylcyclohexanone and 1,741.6 kg/h of high boilers are removed at 88.7° C.

A take-off column having a total of 35 theoretical plates is connected between the lowermost column plate and the 29th theoretical plate. About 4,500 kg/h of liquid from the main column are introduced at the upper end at 66.8° C., and about 4,300 kg/h of vapors from the main column are fed in at the lower end. At the level of the tenth theoretical plate of this column 4 25 kg/h of a medium-boiling fraction are removed in liquid form at 74° C., the said fraction containing 72.2% of cyclohexanone, 21% of cyclohexanol and 6.8% of methylcyclohexanone.

We claim:

1. A process for removing a medium-boiling fraction from a liquid feed mixture consisting essentially of the steps: distilling the liquid feed mixture containing 40 to 65% by weight of cyclohexanone as a low-boiling fraction, methylcyclohexanone as the medium-boiling fraction and from 30 to 60% by weight of cyclohexanol and from 1 to 10% by weight of higher-boiling by-products as a high-boiling fraction; using a distillation column (main column) consisting of a rectifying part and a stripping part, the rectifying part connected by a liquid-phase line so as to pass liquid from said part to the upper end of a second distillation column (side column), and the stripping part connected by a vapor-phase line so as to pass vapor from said part to the lower end of the side column; removing the medium-boiling fraction in vapor or liquid form from the middle section of the side column; removing a cyclohexanone fraction containing from 0.0001 to 0.02% by weight of methylcyclohexanone at the top of the main column; removing a cyclohexanol fraction containing from 0.002 to 0.4% by weight of methylcyclohexanone at the bottom of the main column; and removing a medium-boiling fraction containing from 1 to 25% by weight of methylcyclohexanone at the withdrawal point of the side column; wherein the concentration of the medium-boiling fraction in said liquid feed mixture is less than 2% and the amount of vapor which is passed into the lower end of the side column from the stripping part of the main column is 1-20% based on the amount of vapor in the main column at the point of withdrawal from the stripping part.

2. The process of claim 1, wherein the withdrawal point of the side column is arranged in such a way that the ratio of the number of theoretical plates of the section of the main column between a feed point and the upper connection point to that between the feed point and the lower connection point is equal to the ratio of the numbers of theoretical plates of the sections of the side column below the withdrawal point to those above the withdrawal point.

3. The process of claim 1, wherein the number of theoretical plates of the side column is 100-200% compared with the number of plates in the corresponding section of the main column between the connections with the side column.

4. The process of claim 3, wherein the number of theoretical plates of the side column is 120-140% compared with the number of plates in the corresponding section of the main column between the connection with the side column.

5. The process of claim 1, wherein the liquid removed from the main column is introduced at the upper end of the side column, this amount of liquid corresponding to 100-110% of the amount of vapor in the side column.

6. The process of claim 1, wherein the medium-boiling fraction is removed in the form of a liquid and, at the withdrawal point of the fraction in the side column, an amount of liquid is kept for a residence time of from 0.1 to 2 hours in the column or in a separate container, and a side stream is removed at the withdrawal point only periodically after analysis of the liquid.

7. The process of claim 1, wherein the main column is operated at a top pressure of from 0.01 to 1 bar and with a reflux ratio of from 1.2 to 6.0 the number of theoretical plates of the main column is from 30 to 65 the side column has from 30 to 80 theoretical plates.

8. The process of claim 7, wherein the column is operated at a pressure of from 0.03 to 0.06 bar and with a reflux ratio of 1.8 to 3.0, the number of theoretical plates of the main column is 40 to 50 and the number of theoretical plates of the side column is 30-40.

9. The process of claim 1, wherein the concentration of the medium-boiling fraction in the liquid mixture is less than 0.1%.

10. The process of claim 1, wherein the amount of vapor which is passed into the lower end of the side column from the stripping part of the main column is 3-10% based on the amount of vapor in the main column at the point of withdrawal from the stripping part.

* * * * *